(12) United States Patent
Kendrick et al.

(10) Patent No.: US 7,311,908 B2
(45) Date of Patent: *Dec. 25, 2007

(54) PHARMACEUTICAL COMPOSITIONS OF FIBRINOLYTIC AGENT

(75) Inventors: Brent S. Kendrick, Moorpark, CA (US); Brian A. Peterson, Simi Valley, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/479,214

(22) Filed: Jun. 29, 2006

(65) Prior Publication Data

US 2006/0246053 A1 Nov. 2, 2006

Related U.S. Application Data

(60) Continuation of application No. 10/226,408, filed on Aug. 23, 2002, now Pat. No. 7,138,114, which is a division of application No. 09/411,335, filed on Oct. 1, 1999, now Pat. No. 6,440,414.

(51) Int. Cl.
*A61K 38/46* (2006.01)
(52) U.S. Cl. ..................... 424/94.67; 435/219; 435/226
(58) Field of Classification Search ..................... None
See application file for complete search history.

(56) References Cited

U.S. PATENT DOCUMENTS

| | | | |
|---|---|---|---|
| 4,083,961 | A | 4/1978 | Dussourd'Hinterland et al. |
| 4,447,236 | A | 5/1984 | Quinn |
| 4,610,879 | A | 9/1986 | Markland et al. |
| 4,692,139 | A | 9/1987 | Stiles |
| 4,755,167 | A | 7/1988 | Thistle et al. |
| 4,812,405 | A | 3/1989 | Lair et al. |
| 4,818,700 | A | 4/1989 | Cregg et al. |
| 4,837,148 | A | 6/1989 | Cregg |
| 4,855,231 | A | 8/1989 | Stroman et al. |
| 4,885,242 | A | 12/1989 | Cregg |
| 5,167,628 | A | 12/1992 | Boyles |
| 5,222,941 | A | 6/1993 | Don Michael |
| 5,250,034 | A | 10/1993 | Appling et al. |
| 5,370,653 | A | 12/1994 | Cragg |
| 5,380,273 | A | 1/1995 | Dubrul et al. |
| 5,498,236 | A | 3/1996 | Dubrul et al. |
| 5,626,564 | A | 5/1997 | Zhan et al. |
| 5,709,676 | A | 1/1998 | Alt |
| 5,830,468 | A | 11/1998 | Bini |
| 5,865,178 | A | 2/1999 | Yock |
| 5,922,322 | A | 7/1999 | Bini |
| 5,951,981 | A | 9/1999 | Markland, Jr. et al. |
| 6,020,181 | A | 2/2000 | Bini |
| 6,107,280 | A | 8/2000 | White et al. |
| 6,455,269 | B1 | 9/2002 | Toombs |
| 6,759,431 | B2 | 7/2004 | Hunter et al. ................. 514/449 |
| 2002/0081685 | A1 | 6/2002 | Fox et al. .................... 435/183 |

FOREIGN PATENT DOCUMENTS

| | | |
|---|---|---|
| EP | 0 323 722 | 7/1989 |
| EP | 0 438 200 | 7/1991 |
| EP | 0 624 642 | 11/1994 |
| EP | 0 689 843 | 1/1996 |
| WO | WO 90/07352 | 7/1990 |
| WO | WO 96/36227 | 11/1996 |
| WO | WO 98/24917 | 6/1998 |
| WO | WO 98/46771 | 10/1998 |
| WO | WO 01/24817 | 4/2001 |
| WO | WO 01/25445 | 4/2001 |
| WO | WO 02/12283 A2 | 2/2002 |

OTHER PUBLICATIONS

No authors listed, "Results of a Prospective Randomized Trial Evaluating Surgery Versus Thrombolysis for Ischemia of the Lower Extremity," The Site Trial, Stile Investigators Appendix A, Annals of Surgery, 220(3):251-266 (1994).

Ahmed et al., "Biochemical Characteristics of Fibrolase, a Fibrinolytic Protease From Snake Venom," Haemostasis, 20:147-154 (1990).

Ahmed et al., "Biochemical and Thrombolytic Properties of Fibrolase—A New Fibrinolytic Protease From Snake Venom," Haemostasis, 20:334-340 (1990).

Anai et al., "Inhibition of a Snake Venom Hemorrhagic Metalloproteinase by Human and Rat Alpha-Macroglobulins," Toxicon: Official Journal of the International Society on Toxinology, 36(8):1127-1139 (1998).

Barrett, A.J. (ed) Methods in Enzymology, Academic Press, Inc., Philadelphia, PA, 737-754 (1981).

Bode et al., Astacins, Serralysins, Snake Venom and Matrix Metalloproteinases Exhibit Identical Zinc-Binding Environments (HEXXHXXGXXH and Met-Turn) and Topologies and Should be Grouped Into a Common Family, the 'Metzincins', FEBS Lett., 331(1-2):134-140 (1993).

Carpenter et al., "Interaction of Stabilizing Additives With Proteins During Freeze-Thawing and Freeze-Drying" Develop. Biol. Standard, 74:225-239 (1991).

Chen, Drug Development and Industrial Pharmacy, 18(11 and 12):1311-1354 (1992).

Guan et al., Archives of Biochemistry and Biophysics, 289(2):197-207 (1991).

Jackson and Claggett,"Antithrombotic Therapy in Peripheral Arterial Occlusive Disease," Chect, 114:666S-682S (1998).

Kandarpa et al., "Forceful Pulsatile Local Infusion of Enzyme Accelerates Thrombolysis: In Vivo Evaluation of a New Delivery System," Radiology, 168:739-744 (1981).

(Continued)

*Primary Examiner*—Nashaat T. Nashed
(74) *Attorney, Agent, or Firm*—Robins & Pasternak LLP

(57) ABSTRACT

Frozen and lyophilized compositions for a metalloproteinase fibrinolytic agent (fibrolase or NAT), a method for preparing the lyophilized composition, and a kit and method for reconstituting the lyophilized composition are described herein.

5 Claims, No Drawings

OTHER PUBLICATIONS

Loayza et al., Journal of Chromatography B, pp. 227-243 (1994).

Manning, "Sequence Analysis of Fibrilase, a Fibrinolytic Metalloroteinase From *Agkistrodon contortrix contortrix*," Toxicon, 33(9):1189-1200 (1995).

Markland et al., "Thrombolytic Effects of Recombinant Fibrolase or Apsac in a Canine Model of Carotid Artery Thrombosis," Circulation, 90(5):2448-2456 (1994).

Markland et al., "Resolution of Isoforms of Natural and Recombinant Fibrinolytic Snake Venom Enzyme Using High Performance Capillary Electrophoresis," Journal of Liquid Chromatography, 16(1-10):2189-2201 (1993).

Ouriel et al., "A Comparison of Thrombolytic Therapy With Operative Revascularization in the Initial Treatment of Acute Peripheral Arterial Ischemia," Journal of Vascular Surgery, 19:1021-1030 (1994).

Ouriel et al., "A Comparison of Recombinent Urokinase With Vascular Surgery as Initial Treatment of Acute Arterial Occlusion of the Legs," New England Journal of Medicine, 338:1105-1111 (1998).

Potempa et al., "Stabilization vs. Degradation of *Staphylococcus aureus* Metalloproteinase," Biochimica et Biophysica Acia, 993:301-304 (1989).

Pretzer et al., "Stability of the Thrombolytic Protein Fibrolase: Effect of Temperature and pH on Activity and Conformation," Pharmaceutical Research, 8(9):1103-1112 (1991).

Pretzer et al., "Effect of Zinc Binding on the Structure and Stability of Fibriolase, a Fibrinolytic Protein From Snake Venom," Pharmaceutical Research, 9(7):870-877 (1992).

Randolph et al., Protein Science, Cambridge University Press, pp. 590-600 (1992).

Retzios et al., "Fibrinolytic Enzymes From the Venoms of *Agkistrodon contortrix* and *Crotalus basiliscus*," Thrombosis Research, 74(4):355-367 (1994).

Rholam et al., "Role of Amino Acid Sequences Flanking Dibasic Cleavage Sites in Precursor Proteolytic Processing—The Importance of the First Residue C-Terminal of the Cleavage Sites," European Journal of Biochemistry, 227:707-714 (1995).

Selistre de Araujo et al., "Molecular Cloning and Sequence Analysis of CDNAs for Metalloproteinases From Broad-Banded Copperhead *Agkistrodon contortrix laticinctus*", Archives of Biochemistry and Biophysics 320(1):141-148 (1995).

Sreekrishna et al., "Strategies for Optimal Sysnthesis and Secretion of Heterologous Proteins in the Methylothrophic Yeast Pichis Pastoris," Gene, 190:55-62 (1997).

Stocker et al., "The Metzincins-Topological and Sequential Relations Between the Astacins, Adamalysins, Serralysins, and Matrixins (Collagenases Define a Superfamily of Zinc-Peptidases," Protein Sci., 4(5):823-840 (1995).

Verstraete et al., "Thrombolytic Agents in Development," Drugs, 50(1):29-42 (1995).

Williams et al., "The Lyophilization of Pharmaceuticals: A Literature Review," Journal of Parenteral Science and Technology, 38(2):48-59 (1984).

SEQUENCE LISTING

<160> NUMBER OF SEQ ID NOS: 6

<210> SEQ ID NO 1
<211> LENGTH: 201
<212> TYPE: PRT
<213> ORGANISM: Artificial Sequence
<220> FEATURE:
<223> OTHER INFORMATION: Description of Artificial Sequence: NAT
      (analog of fibrolase of Agkistrodon Contortrix)

<400> SEQUENCE: 1

Ser Phe Pro Gln Arg Tyr Val Gln Leu Val Ile Val Ala Asp His Arg
 1               5                  10                  15

Met Asn Thr Lys Tyr Asn Gly Asp Ser Asp Lys Ile Arg Gln Trp Val
            20                  25                  30

His Gln Ile Val Asn Thr Ile Asn Glu Ile Tyr Arg Pro Leu Asn Ile
        35                  40                  45

Gln Phe Thr Leu Val Gly Leu Glu Ile Trp Ser Asn Gln Asp Leu Ile
    50                  55                  60

Thr Val Thr Ser Val Ser His Asp Thr Leu Ala Ser Phe Gly Asn Trp
65                  70                  75                  80

Arg Glu Thr Asp Leu Leu Arg Arg Gln Arg His Asp Asn Ala Gln Leu
                85                  90                  95

Leu Thr Ala Ile Asp Phe Asp Gly Asp Thr Val Gly Leu Ala Tyr Val
            100                 105                 110

Gly Gly Met Cys Gln Leu Lys His Ser Thr Gly Val Ile Gln Asp His
        115                 120                 125

Ser Ala Ile Asn Leu Leu Val Ala Leu Thr Met Ala His Glu Leu Gly
    130                 135                 140

His Asn Leu Gly Met Asn His Asp Gly Asn Gln Cys His Cys Gly Ala
145                 150                 155                 160

Asn Ser Cys Val Met Ala Ala Met Leu Ser Asp Gln Pro Ser Lys Leu
                165                 170                 175

Phe Ser Asp Cys Ser Lys Lys Asp Tyr Gln Thr Phe Leu Thr Val Asn
            180                 185                 190

Asn Pro Gln Cys Ile Leu Asn Lys Pro
        195                 200

<210> SEQ ID NO 2
<211> LENGTH: 603
<212> TYPE: DNA
<213> ORGANISM: Artificial Sequence
<220> FEATURE:
<223> OTHER INFORMATION: Description of Artificial Sequence: Encodes NAT
      (analog of fibrolase)

<400> SEQUENCE: 2
tctttcccac aaagatacgt acagctggtt atcgttgctg accaccgtat gaacactaaa      60
tacaacggtg actctgacaa aatccgtcaa tgggtgcacc aaatcgtcaa caccattaac     120
gaaatctaca gaccactgaa catccaattc actttggttg gtttggaaat ctggtccaac     180
caagatttga tcaccgttac ttctgtatcc cacgacactc tggcatcctt cggtaactgg     240
cgtgaaaccg acctgctgcg tcgccaacgt catgataacg ctcaactgct gaccgctatc     300
gacttcgacg gtgatactgt tggtctggct tacgttggtg gcatgtgtca actgaaacat     360
tctactggtg ttatccagga ccactccgct attaacctgc tggttgctct gaccatggca     420

```
cacgaactgg gtcataacct gggtatgaac cacgatggca accagtgtca ctgcggtgca    480
aactcctgtg ttatggctgc tatgctgtcc gatcaaccat ccaaactgtt ctccgactgc    540
tctaagaaag actaccagac cttcctgacc gttaacaacc cgcagtgtat cctgaacaaa    600
ccg                                                                  603
```

<210> SEQ ID NO 3
<211> LENGTH: 203
<212> TYPE: PRT
<213> ORGANISM: Agkistrodon contortrix
<220> FEATURE:
<223> OTHER INFORMATION: Native fibrolase of Agkistrodon Contortrix

<400> SEQUENCE: 3

```
Gln Gln Arg Phe Pro Gln Arg Tyr Val Gln Leu Val Ile Val Ala Asp
 1               5                  10                  15

His Arg Met Asn Thr Lys Tyr Asn Gly Asp Ser Asp Lys Ile Arg Gln
            20                  25                  30

Trp Val His Gln Ile Val Asn Thr Ile Asn Glu Ile Tyr Arg Pro Leu
        35                  40                  45

Asn Ile Gln Phe Thr Leu Val Gly Leu Glu Ile Trp Ser Asn Gln Asp
    50                  55                  60

Leu Ile Thr Val Thr Ser Val Ser His Asp Thr Leu Ala Ser Phe Gly
65                  70                  75                  80

Asn Trp Arg Glu Thr Asp Leu Leu Arg Arg Gln Arg His Asp Asn Ala
                85                  90                  95

Gln Leu Leu Thr Ala Ile Asp Phe Asp Gly Asp Thr Val Gly Leu Ala
            100                 105                 110

Tyr Val Gly Gly Met Cys Gln Leu Lys His Ser Thr Gly Val Ile Gln
        115                 120                 125

Asp His Ser Ala Ile Asn Leu Leu Val Ala Leu Thr Met Ala His Glu
    130                 135                 140

Leu Gly His Asn Leu Gly Met Asn His Asp Gly Asn Gln Cys His Cys
145                 150                 155                 160

Gly Ala Asn Ser Cys Val Met Ala Ala Met Leu Ser Asp Gln Pro Ser
                165                 170                 175

Lys Leu Phe Ser Asp Cys Ser Lys Lys Asp Tyr Gln Thr Phe Leu Thr
            180                 185                 190

Val Asn Asn Pro Gln Cys Ile Leu Asn Lys Pro
        195                 200
```

<210> SEQ ID NO 4
<211> LENGTH: 609
<212> TYPE: DNA
<213> ORGANISM: Agkistrodon contortrix
<220> FEATURE:
<223> OTHER INFORMATION: Encodes native fibrolase of Agkistrodon
      Contortrix

<400> SEQUENCE: 4

```
caacaaagat cccacaaag atacgtacag ctggttatcg ttgctgacca ccgtatgaac     60
actaaataca cggtgactc tgacaaaatc cgtcaatggg tgcaccaaat cgtcaacacc    120
attaacgaaa tctacagacc actgaacatc caattcactt tggttggttt ggaaatctgg    180
tccaaccaag atttgatcac cgttacttct gtatcccacg acactctggc atccttcggt    240
aactggcgtg aaaccgacct gctgcgtcgc caacgtcatg ataacgctca actgctgacc    300
gctatcgact cgacggtga tactgttggt ctggcttacg ttggtggcat gtgtcaactg    360
```

-continued

```
aaacattcta ctggtgttat ccaggaccac tccgctatta acctgctggt tgctctgacc      420
atggcacacg aactgggtca taacctgggt atgaaccacg atggcaacca gtgtcactgc      480
ggtgcaaact cctgtgttat ggctgctatg ctgtccgatc aaccatccaa actgttctcc      540
gactgctcta agaaagacta ccagaccttc ctgaccgtta caacccgca gtgtatcctg      600 aacaaaccg                                                              609
```

```
<210> SEQ ID NO 5
<211> LENGTH: 1392
<212> TYPE: DNA
<213> ORGANISM: Agkistrodon contortrix
<220> FEATURE:
<223> OTHER INFORMATION: Native profibrolase of Agkistrodon Contortrix

<400> SEQUENCE: 5
```

```
atgagatttc cttcaattt tactgctgtt ttattcgcag catcctccgc attagctgct      60
ccagtcaaca ctacaacaga agatgaaacg gcacaaattc cggctgaagc tgtcatcggt    120
tactcagatt tagaagggga tttcgatgtt gctgttttgc catttttccaa cagcacaaat   180 aacgggttat tgtttataaa tactactatt gccagcattg ctgctaaaga agaagggggta  240 tctctcgaga aaagagaggc tgaagcttct tctattatct tggaatctgg taacgttaac   300
gattacgaag ttgttttatcc aagaaaggtc actccagttc ctaggggtgc tgttcaacca  360
aagtacgaag atgccatgca atacgaattc aaggttaaca gtgaaccagt tgtcttgcac   420
ttggaaaaaa acaaaggttt gttctctgaa gattactctg aaactcatta ctccccagat   480
ggtagagaaa ttactactta cccattgggt gaagatcact gttactacca tggtagaatc   540
gaaaacgatg ctgactccac tgcttctatc tctgcttgta cggtttgaa gggtcatttc    600 aagttgcaag gtgaaatgta cttgattgaa ccattggaat tgtccgactc tgaagcccat   660
gctgtctaca gtacgaaaa cgtcgaaaag gaagatgaag ccccaaagat gtgtggtgtt    720 acccaaaaact gggaatcata tgaaccaatc aagaaggcct tccaattaaa cttgactaag   780
agacaacaaa gattcccaca agatacgta cagctggtta tcgttgctga ccaccgtatg    840
aacactaaat acaacggtga ctctgacaaa atccgtcaat gggtgcacca aatcgtcaac   900
accattaacg aaatctacag accactgaac atccaattca ctttggttgg tttgaaaatc   960
tggtccaacc aagatttgat caccgttact tctgtatccc acgacactct ggcatccttc   1020
ggtaactggc gtgaaaccga cctgctgcgt cgccaacgtc atgataacgc tcaactgctg   1080
accgctatcg acttcgacgg tgatactgtt ggtctggctt acgttggtgg catgtgtcaa   1140
ctgaaacatt ctactggtgt tatccaggac cactccgcta ttaacctgct ggttgctctg   1200
accatggcac acgaactggg tcataacctg gtatgaacc acgatggcaa ccagtgtcac   1260
tgcggtgcaa actcctgtgt tatggctgct atgctgtccg atcaaccatc caaactgttc  1320
tccgactgct ctaagaaaga ctaccagacc ttcctgaccg ttaacaaccc gcagtgtatc   1380
ctgaacaaac cg                                                        1392
```

```
<210> SEQ ID NO 6
<211> LENGTH: 1386
<212> TYPE: DNA
<213> ORGANISM: Artificial Sequence
<220> FEATURE:
<223> OTHER INFORMATION: Description of Artificial Sequence: proNAT
      (analog of profibrolase of Agkistrodon Contortrix

<400> SEQUENCE: 6
```

-continued

```
atgagatttc cttcaatttt tactgctgtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc cattttccaa cagcacaaat       180
aacgggttat tgtttataaa tactactatt gccagcattg ctgctaaaga agaagggta        240 tctctcgaga aaagagaggc tgaagcttct tctattatct tggaatctgg taacgttaac       300
gattacgaag ttgtttatcc aagaaaggtc actccagttc ctagggggtgc tgttcaacca      360 aagtacgaag atgccatgca atacgaattc aaggttaaca gtgaaccagt tgtcttgcac       420
ttggaaaaaa acaaaggttt gttctctgaa gattactctg aaactcatta ctccccagat       480
ggtagagaaa ttactactta cccattgggt gaagatcact gttactacca tggtagaatc       540
gaaaacgatg ctgactccac tgcttctatc tctgcttgta acggtttgaa gggtcatttc       600
aagttgcaag gtgaaatgta cttgattgaa ccattggaat tgtccgactc tgaagcccat       660
gctgtctaca agtacgaaaa cgtcgaaaag gaagatgaag ccccaaagat gtgtggtgtt       720
acccaaaact gggaatcata tgaaccaatc aagaaggcct tccaattaaa cttgactaag       780
agatctttcc cacaaagata cgtacagctg gttatcgttg ctgaccaccg tatgaacact       840
aaatacaacg gtgactctga caaaatccgt caatgggtgc accaaatcgt caacaccatt       900
aacgaaatct acagaccact gaacatccaa ttcactttgg ttggtttgga aatctggtcc       960
aaccaagatt tgatcaccgt tacttctgta tcccacgaca ctctggcatc cttcggtaac      1020
tggcgtgaaa ccgacctgct gcgtcgccaa cgtcatgata acgctcaact gctgaccgct      1080
atcgacttcg acggtgatac tgttggtctg gcttacgttg gtggcatgtg tcaactgaaa      1140
cattctactg gtgttatcca ggaccactcc gctattaacc tgctggttgc tctgaccatg      1200
gcacacgaac tgggtcataa cctgggtatg aaccacgatg gcaaccagtg tcactgcggt      1260
gcaaactcct gtgttatggc tgctatgctg tccgatcaac catccaaact gttctccgac      1320
tgctctaaga aagactacca gaccttcctg accgttaaca acccgcagtg tatcctgaac      1380
aaaccg                                                                 1386
```

PHARMACEUTICAL COMPOSITIONS OF FIBRINOLYTIC AGENT

CROSS-REFERENCE TO RELATED APPLICATIONS

This application is a continuation application of U.S. Ser. No. 10/226,408, filed Aug. 23, 2002, now U.S. Pat. No. 7,138,114, which is a divisional application of U.S. Ser. No. 09/411,335, filed Oct. 1, 1999, now U.S. Pat. No. 6,440,414, from which applications priority is claimed pursuant to 35 U.S.C. §120, and which applications are incorporated herein by reference in their entireties.

FIELD OF THE INVENTION

The present invention relates to novel pharmaceutical compositions of a fibrinolytic agent. More specifically, the present invention relates to frozen liquid and lyophilized compositions of fibrolase and, separately, of "novel acting thrombolytic" (NAT) (SEQ ID NO:1), as well as methods for the production and use thereof.

BACKGROUND OF THE INVENTION

In general, polypeptides are marginally stable in the aqueous state and undergo chemical and physical degradation resulting in a loss of biological activity during processing and storage. Another problem encountered in aqueous solution in particular is hydrolysis, such as deamidation and peptide bond cleavage. These effects represent a serious problem for therapeutically active polypeptides which are intended to be administered to humans within a defined dosage range based on biological activity.

To reduce the degradation of polypeptides, water-based pharmaceutical compositions are generally kept refrigerated or frozen until ready for use. As an alternative, the process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984).

In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Lyophilization is considered one of the best ways to remove excess water from polypeptide solutions. The freeze-drying process may yield products that are stable and amenable to handling for long-term storage. Lyophilized products can be stored at room temperature and are therefore easier to handle and distribute to a wider geographic market, such as foreign markets where refrigeration may not be available.

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

SUMMARY OF THE INVENTION

The present invention relates to stable pharmaceutical compositions of fibrolase and "novel acting thrombolytic" (NAT) (SEQ ID NO:1), some of which are liquid compositions suitable for storage in the frozen state, and others of which are suitable for lyophilization.

Because of the fibrinolytic properties of fibrolase and NAT (SEQ ID NO:1), the compositions of this invention are useful to lyse blood clots in vivo and may be administered therapeutically for such a purpose.

For purposes of this invention, the term "NAT" refers to the metalloproteinase having fibrinolytic activity which is characterized by SEQ ID NO: 1. The NAT polypeptide is encoded by the cDNA molecule of SEQ ID NO: 2, although any DNA molecule of variant sequence encoding the same polypeptide may be used for expression and manufacture in accordance with methods which are referred to hereinbelow.

Fibrolase is a known metalloproteinase which has been described in the scientific and patent literature; see Randolph et al., Protein Science, Cambridge University Press (1992), pages 590-600, and European patent Application No. 0 323 722 (Valenzuela et al.), published Jul. 12, 1989. Typically, the fibrolase employed in the compositions of this invention will be of SEQ ID NO: 3, which is encoded by the cDNA molecule of SEQ ID NO: 4 (or variants thereof encoding the same amino acid sequence).

Fibrolase and NAT (SEQ ID NO:1) are to be distinguished from other therapeutic agents for the treatment of blood clots in vivo, such as urokinase, streptokinase and tPA which are plasminogen activators. Unlike these other agents, fibrolase and NAT (SEQ ID NO:1) act directly on the clot to degrade both fibrin and fibrinogen.

The pharmaceutical compositions of this invention will contain, in addition to a therapeutically effective amount of fibrolase or NAT (SEQ ID NO: 1), a zinc stabilizer and, optionally, a bulking agent with or without other excipients in a pharmaceutically-acceptable buffer which, in combination, provide a stable, frozen or lyophilized product that can be stored for an extended period of time.

In one of its aspects, the present invention provides a freezable liquid medicinal composition comprising fibrolase or NAT (SEQ ID NO:1), a water soluble zinc salt, a citric acid buffer, optionally an additional stabilizer selected from the group consisting of water soluble calcium salts, and optionally a bulking agent (for example, mannitol). A surfactant, such as TWEEN 80 (BASF, Gumee, Ill.), may also be added to increase freeze-thaw stability. Tris buffer (Sigma, St. Louis, Mo.) or another buffer with a buffer capacity above pH 7.0 may be added to stabilize the pH at or above pH 7.4.

In another aspect of the present invention, the pharmaceutical composition can be a lyophilizable or lyophilized pharmaceutical composition comprising fibrolase or NAT (SEQ ID NO:1), a zinc stabilizer (e.g., water soluble zinc salt), and a citric acid buffer, with or without other excipients (e.g., bulking agent such as mannitol, glycine, or the like). The lyophilized composition may also contain a disaccharide sugar, such as sucrose or trehalose, as a lyoprotectant. A surfactant, such as TWEEN 80, may be added to protect against lyophilization stresses on the metalloproteinase (fibrolase or NAT (SEQ ID NO:1)). The pH will ideally be maintained at pH 8.0±0.5, using a suitable buffer with a p$K_a$ in this range (for example, Tris).

The invention also comprises a method for preparing a lyophilized composition, comprising the steps of (i) mixing fibrolase or NAT (SEQ ID NO:1) with a buffer and a water soluble zinc salt, as well as any desired optional ingredients, and (ii) lyophilizing this mixture.

In addition, the invention provides a kit for preparing an aqueous pharmaceutical composition, comprising a first container having the aforementioned lyophilized composition and a second container having a physiologically acceptable solvent therefor.

Still another aspect of this invention comprises a method comprising the steps of reconstituting the lyophilized composition and administering the reconstituted composition to a patient in need of blood clot lysis.

DETAILED DESCRIPTION OF THE INVENTION

A variety of host-vector systems may be utilized to express the coding sequence for fibrolase or NAT polypeptide in accordance with standard methods for recombinant expression which are well known to those skilled in the art, and thereby obtain the fibrinolytically active polypeptide for the compositions. Such systems include, but are not limited to, eukaryotic cell systems such as mammalian cell systems infected with virus (for example, vaccinia virus, adenovirus, etc.); insect cell systems infected with virus (for example, baculovirus); microorganisms such as yeast containing yeast vectors; or prokaryotic cell systems such as bacteria (e.g., *E. coli*) transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Preferably, a yeast expression system (e.g., *Pichia pastoris*) is employed for recombinant expression because of its greater efficiency. A detailed description of such a system may be found in U.S. Pat. No. 4,855,231 (Stroman et al.), U.S. Pat. No. 4,812,405 (Lair et al.), U.S. Pat. No. 4,818,700 (Cregg et al.), U.S. Pat. No. 4,885,242 (Cregg), and U.S. Pat. No. 4,837,148 (Cregg), the disclosures of which are hereby incorporated by reference. Expression of fibrolase in such a system will typically involve a DNA molecule of SEQ ID NO: 5, which encodes "prepro" sequence (nucleotides 1-783) in addition to the "mature" polypeptide (nucleotides 784-1392). Expression of NAT in such a system will typically involve a DNA molecule of SEQ ID NO: 6, which encodes "prepro" sequence (nucleotides 1-783) in addition to the "mature" polypeptide (nucleotides 784-1386).

Further details regarding NAT (SEQ ID NO:1) and methods for its preparation may be found in commonly assigned copending patent application Ser. No. 09/411,329, now U.S. Pat. No. 6,261,820, filed concurrently herewith, which is hereby incorporated by reference.

Once the polypeptide (fibrolase or NAT (SEQ ID NO:1)) has been prepared, purified, and then assayed for activity (using procedures for fibrinolytic agents known to those skilled in the art), it may be formulated into pharmaceutical compositions in accordance with this invention.

In the present compositions (whether frozen or lyophilized), a stabilizer (which can also be referred to as a "glass-forming additive") is added to prevent or reduce precipitation and chemical degradation of fibrolase or NAT (SEQ ID NO:1), whichever the case may be. A hazy or turbid solution at room temperature indicates that the polypeptide has precipitated. The term "stabilizer" means an excipient capable of preventing aggregation or other physical degradation, as well as chemical degradation (for example, autolysis, deamidation, oxidation, etc.) of fibrolase or NAT (SEQ ID NO:1) in an aqueous medium.

It has been found that the incorporation of a zinc stabilizer, and more specifically a water soluble zinc salt, increases the stability of the metalloproteinase (fibrolase or NAT (SEQ ID NO:1)) in each type of composition, as compared to formulations in which inorganic or other types of organic compounds are used to prevent aggregation and/or polypeptide decomposition. Specifically, zinc concentrations above 0.01 millimolar (mM) will stabilize the metalloproteinase, with the proviso that zinc concentrations above 1 mM significantly limit the solubility of fibrolase or NAT (SEQ ID NO:1). Thus, a range from about 0.01 mM to about 1 mM is advised. Examples of suitable zinc salts are zinc acetate, zinc sulfate and zinc chloride.

Frozen liquid compositions in accordance with this invention, in particular, may optionally (but not necessarily) also include a water soluble calcium salt as an additional stabilizer. Examples are calcium acetate, calcium sulfate or calcium chloride, which are preferably present in a concentration from about 0.001 to about 0.02 mM, and more preferably at a concentration of about 0.01±0.002 mM.

If desired, other stabilizers that are conventionally employed in pharmaceutical compositions, such sucrose, trehalose or glycine, may be used in addition to the above mentioned. Typically, such stabilizers will be added in minor amounts ranging from, for example, about 0.1% to about 0.5% (w/v). Surfactant stabilizers, such as Tween 20 or Tween 80 (BASF), may also be added in conventional amounts.

If desired, the frozen liquid and lyophilized compositions can also include a bulking/osmolarity regulating agent. Preferably, mannitol is incorporated in a concentration of about 2% to about 8% weight by volume (w/v), and usually at a concentration of about 5% (w/v).

The choice of a pharmaceutically-acceptable buffer and pH has also been found to affect the stability of the present compositions. Fibrolase or NAT (SEQ ID NO:1) is most stable above a neutral pH (7.0). Significant precipitation of either metalloproteinase occurs at a pH below 7.0 when the frozen composition is thawed or the lyophilized composition is reconstituted. The buffer system present in the compositions is selected to be physiologically compatible and to maintain a desired pH in the reconstituted solution as well as in the solution before lyophilization. Preferably, the buffers have a pH buffering capacity in the range of from about pH 7.0 to about pH 8.5.

Specifically, citric acid buffers (i.e., citric acid or a citric acid salt) are preferably incorporated in a concentration of about 20 mM to about 110 mM, and most preferably at about 100 mM in the frozen liquid composition and about 20 mM in the lyophilized composition. Citric acid salts are used as both buffering agents and stabilizing agents in the compositions of this invention. Whether an acid form itself or a salt thereof is used, the citric acid buffer will be chosen to adjust the pH of the composition to a value within the desired range as indicated above (in the case of the lyophilized composition, after reconstitution). Additional buffering agents, such as Tris, may be added in suitably effective amounts to maintain an adequate buffering capacity above pH 7.0.

A preferred liquid composition to be frozen will contain, in addition to solubilized fibrolase or NAT (SEQ ID NO:1), zinc acetate in a concentration of about 0.08 mM to about 0.12 mM, calcium acetate in a concentration of about 0.008 mM to about 0.012 mM, and citric acid (or sodium citrate) in a concentration of about 95 mM to about 105 mM, at about pH 7.4. Another preferred liquid composition will contain fibrolase or NAT (SEQ ID NO:1), zinc acetate in a concentration of about 0.08 mM to about 0.12 mM, citric acid (or sodium citrate) in a concentration of about 18 mM to about 22 mM, Tris in a concentration of about 0.02 mM to about 0.06 mM, mannitol in a concentration of about 3% to about 6% (w/v), and TWEEN 80 in a concentration of about 0.008% to about 0.012% (w/v), at apH of about 8.0.

A preferred lyophilizable composition will contain, in addition to fibrolase or NAT (SEQ ID NO:1), zinc sulfate in a concentration of about 0.08 mM to about 0.12 mM, citric acid (or sodium citrate) in a concentration of about 18 mM to about 22 mM, Tris in a concentration of about 3 mM to about 6 mM, mannitol in a concentration of about 3% to about 6% (w/v), and TWEEN 80 in a concentration of about 0.008% to about 0.012% (w/v), at apH of about 8.0.

For all compositions in accordance with this invention, fibrolase or NAT is present in a concentration of about 0.1 mg/ml to about 50 mg/ml, preferably, with a concentration of about 5 mg/ml to about 40 mg/ml being more preferred, and a concentration of about 10 mg/ml to about 15 mg/ml being the most preferred.

The relative proportions of the excipients in these compositions will depend on several factors. For example, the amount of the metalloproteinase and bulking agent (e.g., mannitol) has an effect on the amount of zinc (and calcium, if present) needed to stabilize the composition. The amount of stabilizer used in the compositions will depend on the amount needed to maintain the structural integrity of fibrolase or NAT (SEQ ID NO:1) during lyophilization or other processing or upon storage.

Still other excipients known in the art can also be included in the composition, provided they are physiologically compatible and are in no way detrimental to fibrolase or NAT (SEQ ID NO:1). For example, the composition may contain minor amounts of additives, such as preservatives, tonicity-adjusting agents, anti-oxidants, or other polymers (for example, viscosity adjusting agents or extenders). Those skilled in the art can readily determine appropriate reagents that would be pharmaceutically useful, based on knowledge of and experience with other pharmaceutical compositions. See, for example, Remington's Pharmaceutical Sciences (latest edition), Mack Publishing Company, Easton, Pa.

The compositions are expected to be stable for at least two years at −30° C. for the frozen composition, and two years at 2° C. to 8° C. for the lyophilized composition. This long-term stability is beneficial for extending the shelf life of the pharmaceutical product and for long distance shipments.

In another aspect, the present invention also provides a method for preparing a lyophilized composition comprising the steps of:

(a) adjusting the pH of a mixture containing the composition ingredients without fibrolase or NAT to between pH 7.6 and pH 8.2, (b) buffer exchanging a fibrolase or NAT containing solution into the composition solution of step (a) and then adding an effective amount of surfactant, and (c) lyophilizing the mixture of step (b).

Fibrolase or NAT (SEQ ID NO:1) and effective amounts of the excipients are admixed under conditions effective to reduce aggregation of the dried fibrolase or NAT (SEQ ID NO:1) polypeptide upon reconstitution with the reconstitution medium, e.g., a solvent which is compatible with the selected administration route and does not negatively interfere with the metalloproteinase, such as sterile water, physiological saline solution, glucose solution or other aqueous solvents (e.g., alcohols such as ethyl, n-propyl or isopropyl, butyl alcohol or mixtures thereof) and, optionally, other components such as antibacterial agents.

The excipients may be admixed with the metalloproteinase at a suitable time before lyophilization. The time taken to mix the excipients and metalloproteinase should be for a sufficient period to prepare a suitable admixture; preferably, mixing will be carried out from about one to about thirty minutes.

Thereafter, the formulated metalloproteinase may be lyophilized, stored and reconstituted using standard methods; see Pikal, supra. The specific conditions under which fibrolase or NAT (SEQ ID NO:1) is freeze-dried and reconstituted are not particularly critical, provided that the conditions selected do not degrade the metalloproteinase and not be deleterious to the stabilizer. A preferred lyophilization cycle comprises freezing the composition at −40° C., annealing the frozen sample at −12° C., and conducting the primary drying at −30° C. to −35° C. for twenty to fifty hours and secondary drying at 20° C. for twenty to forty hours. Generally, the reconstituted composition will be used soon after reconstitution.

Both NAT (SEQ ID NO:1) and fibrolase are best delivered locally to the site of the clot for most effective treatment. Like fibrolase, NAT (SEQ ID NO:1) is covalently bound by $\alpha_2$ macroglobulin in the general circulation. While complexed with $\alpha_2$ macroglobulin, neither fibrolase nor NAT (SEQ ID NO:1) can access the target substrate (i.e., fibrin or fibrinogen) and are largely ineffective unless and until the maximum innate levels of $\alpha_2$ macroglobulin are exceeded. Thus, it is preferred that the compositions of this invention be administered directly to the blood clot via intraarterial or intravenous catheterization.

Description of Specific Embodiments

The following examples further illustrate of the present invention.

The recombinant NAT (SEQ ID NO: 1) used in Examples 1-3 was produced by expression in *P. pastoris* Details regarding a suitable expression system and method may be found in the Stroman et al., Lair et al., Cregg et al. and Cregg patents referred to above. All chemicals were either analytical or USP grade.

EXAMPLE 1

Preparation of Frozen Liquid Composition

An aqueous solution containing 100 mM of citric acid, 0.01 mM of calcium acetate and 0.1 mM of zinc sulfate is prepared by admixture of the ingredients, with the pH adjusted to 7.4. An NAT-containing solution is buffer exchanged into the solution by dialysis (alternatively, ultrafiltration can be used). The resulting NAT solution is concentrated to 10 mg/ml and stored frozen at a temperature of −30° C. until ready for use.

EXAMPLE 2

Preparation of Lyophilized Composition

Preparation of lyophilizable composition. An aqueous solution containing 5 mM of Tris, 20 mm of citric acid, 5% (w/v) of mannitol, 0.5% (w/v) of sucrose and 0.1 mm of zinc sulfate was prepared by admixture of the ingredients, with the pH adjusted to 8.0. A NAT (SEQ ID NO:1) containing solution was buffer exchanged into the composition solution by dialysis (ultrafiltration can be used instead). The resulting NAT solution was concentrated to 10 to 12 mg/ml. TWEEN 80 was added to a final concentration of 0.01% (w/v). The solution was stored at a temperature of 2-8° C. until ready for lyophilization.

Freeze-drying cycle for lyophilized product. The above-prepared composition was first frozen at a temperature of −40° C. in the lyophilizer. The annealing temperature was set at −12° C.; the primary drying temperature was set at −30° C.; and the secondary drying temperature was set at 20° C. The resulting freeze-dried cake showed good morphology and contained less than 3% water, as detected by the Karl Fischer titration method; see Fischer, *Angew Chemie*, Volume 48, page 394 (1935). After the freeze-drying process was finished, the lyophilized cake was put into vials and rubber stoppers were sealed completely under vacuum by pressing down the upper metal shelves in the lyophilizer. The vials were then crimped with 13-mm flip-off aluminum seals and placed in incubators set at different temperatures.

EXAMPLE 3

Analyses of Reconstituted Lyophilized Samples

Sample time points analysis. Sample vials were withdrawn from incubators at predetermined time intervals for the time points analysis. The lyophilized sample cake was first reconstituted by 0.9 ml of sterile water, i.e., "water-for-injection" (McGaw Inc., Irvine, Calif.). Clarity of the reconstituted sample solutions was visually examined. The filtered solution was analyzed by HPLC, UV-Vis spectroscopy and enzyme activity in order to quantify the remaining soluble NAT in these lyophilized samples.

Based on the above analyses, greater than 90% of NAT was recovered after reconstitution of the lyophilized product.

UV/Vis absorbence. 150-200 µl of NAT solution was loaded into a quartz glass SUPRASIL 1-cm path length ultra-microcell. UV/Vis absorbence was measured on an HP 8452A diode-array spectrophotometer (Hewlett-Packard Co., Wilmington, Del.). NAT concentrations were determined using $A^{0.1\%}=1.05$ at 280 nm, based on calculation from the amino acid composition; for reference, see Edelhoch, *Biochemistry*, Volume 6, pages 1948-1954 (1967).

After rehydration of the lyophilized product, no detectable turbidity was observed when measuring the absorbence at 350 nanometers (nm).

High performance liquid chromatography. HPLC analyses of NAT samples were performed using an HP 1050 liquid chromatography system equipped with an HP 3D Chemstation for data acquisition (Hewlett-Packard Co.). NAT species were detected by absorbence at 280 nm and 214 nm using an HP diode-array detector.

For reversed-phase HPLC (RP-HPLC), samples were injected onto a ZORBAX 300SB-C8 column (4.6×250 mm) (Hewlett-Packard Co.) in a mobile phase consisting of 51.5% buffer A (2% isopropanol, 0.1% TFA) and 48.5% buffer B (90% acetonitrile, 2% isopropanol, 0.1% TFA) at a flow rate of 0.6 ml/mm. Buffer B was held for six minutes and then ramped up to 51% over twenty minutes. This concentration was held for one minute, followed by an eight-minute ramp and five-minute hold at 90%. Finally, buffer B was ramped back to 48.5% over a period of three minutes. Recovery of NAT (SEQ ID NO:1) after lyophilization as detected by this method was greater than 92%.

For ion-exchange HPLC (IEX-HPLC), samples were injected onto a Tosohaas DEAE-5PW column (7.5×75 mm) (Tosohaas, Montgomeryville, Ala.) in a mobile phase consisting of 90% buffer A (20 mM Tris, pH 8.5) and 10% buffer B (20 mM Tris, 250 mM NaCl, pH 8.5) at a flow rate of 0.5 ml/mm. Then a gradient was applied, increasing from 10% buffer B to 75% buffer B in 20 minutes, then from 75% B to 90% buffer B in one minute. Buffer B was then held for five minutes, followed by a ramp to 10% buffer B in four minutes. Recovery of NAT (SEQ ID NO:1) after lyophilization as detected by this method was greater than 90%.

For size-exclusion HPLC (SEC-HPLC), samples were loaded into a Tosohaas G-2000SWXL colunm (300×7.8 mm). Isocratic elution was applied at a flow rate of 0.8 ml/mm using a buffer containing 15 mM sodium phosphate, pH 7.0, and 0.140 M sodium chloride. Recovery of NAT (SEQ ID NO:1) after lyophilization as detected by this method was greater than 95%.

Bioassay. Samples were screened for activity against fibrin clots. Small aliquots of a serial dilution of NAT ranging from 0.01 to 1.0 mg/ml were loaded onto preformed fibrin clots in 96-well plates. The samples were incubated for eighteen hours, and clot lysis was quantitated by absorbence at 500 nm. A plot of absorbence vs. NAT concentration for various formulations were compared to a prepared NAT standard for relative activity. There was no measurable difference in the fibrinolytic activity of the NAT after lyophilization, relative to the control (non-lyophilized) sample.

Similar test results are obtained with the frozen liquid composition as well, after the latter is thawed at 4° C. and tested using these same protocols.

The foregoing invention has been described in some detail for purposes of clarity and understanding. It will also be obvious that various other combinations in form and detail can be made without departing from the scope of the invention as defined in the appended claims.

EXAMPLE 4

The procedures of Examples 1 and 2 are repeated with recombinant fibrolase in place of NAT to produce similar frozen liquid and lyohilized pharmaceutical compositions.

The invention claimed is:

1. A composition comprising a therapeutically effective amount of the amino acid sequence of SEQ ID NO:1 and a pharmaceutically acceptable buffer.

2. The composition of claim 1, wherein the composition is an aqueous composition comprising about 10 mg/ml of the polypeptide of SEQ ID NO:1, about 100 mM sodium citrate, about 0.01 mM to about 1 mM zinc acetate, 0.01 mM plus or minus 0.002 mM calcium acetate, with the pH of said composition being about 7.4.

3. The composition of claim 2, wherein the composition consists essentially of 10 mg/ml of the polypeptide of SEQ ID NO:1, 100 mM sodium citrate, 0.10 mM zinc acetate, 0.01 mM plus or minus 0.002 mM calcium acetate, with the pH of said composition being pH 7.4.

4. The composition of claim 1, wherein the composition is lyophilizable and comprises about 10 mg/ml of the polypeptide of SEQ ID NO:1, about 5% (w/v) of mannitol, about 0.5% (w/v) of sucrose, about 20 mM sodium citrate, about 5 mM Tris, about 0.1 mM zinc sulfate, about 0.01% (w/v) TWEEN 80, with the pH of said composition being pH 8 plus or minus 0.5.

5. The composition of claim 4, wherein the composition is lyophilizable and consists essentially of 10 mg/ml of the polypeptide of SEQ ID NO:1, 5% (w/v) of mannitol, 0.5% (w/v) of sucrose, 20 mM sodium citrate, 5 mM Tris, 0.1 mM zinc sulfate, 0.01% (w/v) TWEEN 80, with the pH of said composition being pH 7.9.

* * * * *